(12) United States Patent
Harada et al.

(10) Patent No.: US 6,630,591 B2
(45) Date of Patent: Oct. 7, 2003

(54) PROCESS FOR THE PREPARATION OF QUINOLYLPROPENAL

(75) Inventors: Katsumasa Harada, Yamaguchi (JP); Shigeyoshi Nishino, Yamaguchi (JP); Hidetaka Shima, Yamaguchi (JP); Takashi Harada, Yamaguchi (JP); Naoako Okada, Yamaguchi (JP)

(73) Assignees: Ube Industries, Ltd. (JP); Nissan Chemical Industries, Ltd. (JP)

( * ) Notice: Subject to any disclaimer, the term of this patent is extended or adjusted under 35 U.S.C. 154(b) by 0 days.

(21) Appl. No.: 10/181,820

(22) PCT Filed: Jan. 24, 2001

(86) PCT No.: PCT/JP01/00452
§ 371 (c)(1),
(2), (4) Date: Nov. 20, 2002

(87) PCT Pub. No.: WO01/53265
PCT Pub. Date: Jul. 26, 2001

(65) Prior Publication Data
US 2003/0114680 A1 Jun. 19, 2003

(30) Foreign Application Priority Data

Jan. 24, 2000 (JP) .......................................... 2000-014848
Jan. 24, 2000 (JP) .......................................... 2000-014849

(51) Int. Cl.$^7$ ...................... C07D 215/04; C07D 215/12
(52) U.S. Cl. ...................... 546/173; 546/152; 546/176; 546/180
(58) Field of Search ................................ 546/173, 176, 546/180

(56) References Cited

U.S. PATENT DOCUMENTS 6,335,449 B1 * 1/2002 Ohara et al. ................. 546/173

* cited by examiner

*Primary Examiner*—Charanjit S. Aulakh
(74) *Attorney, Agent, or Firm*—Nixon Peabody LLP; Jeffrey L. Costellia

(57) ABSTRACT

3-[2-Cyclopropyl-4-(4-fluorophenyl)-3 quinolyl]prop-2-enal is prepared in a high yield by reducing 3-[2-cyclopropyl-4-(4-fluorophenyl)-3-quinolyl]prop-2-enenitrile with Raney nickel either in the presence of formic acid and 0.25 to 1 part by volume of water per part by volume of formic acid or in the presence of both an amine salt of formic acid and an organic acid.

9 Claims, No Drawings

PROCESS FOR THE PREPARATION OF QUINOLYLPROPENAL

This application is a 371 of PCT/JP01/00452 filed Jan. 24, 2001, now WO 01/53265 Jan. 26, 2001.

TECNICAL FIELD

The present invention relates to a process for preparing a quinolylpropenal derivative from a quinolyl-acrylonitrile derivative. The quinolylpropenal derivative prepared by the method of the invention is utilizable as an intermediate compound for the synthesis of a cholesterol reducing agent (HMG-CoA reductase inhibitor).

BACKGROUND ART

Until now, it has been known that the quinolylpropenal derivative is prepared by the two step process comprising a step of reducing a quinoline acrylate by diisobutylaluminum hydride to give quinolylpropenol and a subsequent step of oxidizing the quinolylpropenol by the use of a combination of oxalyl chloride and dimethylsulf-oxide, or manganese dioxide (J. Med. Chem., 34, 367 (1991)).

Further known is a method of selectively reducing the cyano group to a formyl group by the use of a diisobutyla-luminum hydride reducing agent, keeping the double bond of an acrylonitrile compound to produce a propenal compound (Heterocycles, 29, 691(1989)).

Both of the above-mentioned process and method are disadvantageous from the viewpoint of industrial preparation because these process and method utilize diisobutyla-luminum hydride or manganese dioxide which requires careful handling procedures and complicated post-treatment.

DISCLOSURE OF THE INVENTION

The present invention resides in a method for preparing 3-[2-cyclopropyl-4-(4-fluorophenyl)-3-quinolyl]-prop-2-enal by reducing 3-[2-cyclopropyl-4-(4-fluoro-phenyl)-3-quinolyl]prop-2-enenitrile using Raney-nickel in the presence of formic acid and water in an amount of 0.25 to 1 volume part per one volume part of the formic acid, or in the presence of an amine salt of formic acid and an organic acid.

The starting compound of the reaction of the invention, that is, 3-[2-cyclopropyl-4-(4-fluorophenyl)-3-quinolyl]prop-2-enenitrile [hereinafter referred to as quinolylacry-lonitrile derivative] and the desired compound, that is, 3-[2-cyclopropyl-4-(4-fluorophenyl)-3-quinolyl]prop-2-enal [hereinafter referred to as quinol-ylpropenal derivative] are the compounds represented, respectively, by the following formulas (1) and (2):

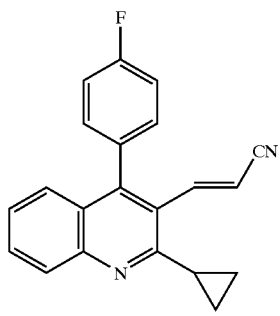
(1)

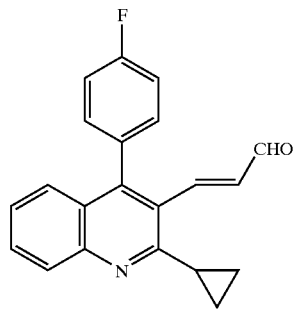
(2)

DETAILED DESCRIPTION OF THE INVENTION

The quinolylacrylonitrile derivative of the formula (1) which is the starting material of the reaction of the invention is new and can be prepared by reacting a known 2-cyclopropyl-4-(4-fluorophenyl)quinoline-3-carbaldehyde (which is described in JP-A-279866, EP-A-304063, and USP 5,011,930) with diethyl cyanomethylphosphonate, preferably in such as solvent as an aromatic hydrocarbon in the presence of a base such as sodium hydroxide.

The Raney-nickel which is employed in the reductive reaction of the invention is an alloy comprising nickel and aluminum as principle ingredients. The nickel content preferably is in the range of 10 to 90 wt. %, more preferably 40 to 80 wt. %. Generally, an activated Raney-nickel is employed. However, Raney-nickels which are pre-treated or stabilized by various methods can be also employed. The Raney-nickel can further comprise other metals such as cobalt, iron, lead, chromium, titan, molybdenum, vanadium, manganese, tin, and tungsten.

In the reducing reaction of the invention, the Raney-nickel is employed in an amount of preferably 0.30 to 2 weight parts in terms of weight of nickel atom, more preferably 0.30 to 1.2 weight parts, per one weight part of the starting compound (i.e., quinolylacrylonitrile derivative).

In one embodiment of the reducing reaction using Raney-nickel can be performed in the presence of formic acid and water in an amount of 0.25 to 1 volume part per one volume part of the formic acid.

According to the study of the present inventors, it has been confirmed that the desired quinolylpropenal derivative of the aforementioned formula (2) can be obtained in a high yield and under easily controllable reaction conditions if the water is used in an amount of the above-mentioned range.

The formic acid is employed in an amount of preferably 0.25 to 50 weight parts, more preferably 1 to 40 weight parts, per one weight part of the quinolylacrylonitrile (starting compound).

When the reducing reaction is carried out, solvents other than formic acid and water can be present in the reaction mixture. There are no specific limitations with respect to the solvents, provided that the solvents do not disturb the reaction. Examples of the solvents include amides such as N,N-dimethylformamide; alcohols such as methanol, ethanol, isopropyl alcohol, and t-butyl alcohol; ketones such as acetone and methyl ethyl ketone; aliphatic hydrocarbons such as pentane and cyclohexane; and aromatic hydrocarbons such as toluene and xylene.

If the above-mentioned solvent is employed in the reducing reaction, the solvent is employed in an amount of generally, not more than 60 weight parts, particularly not more than 10 weight parts, per one weight part of the quinolylacrylonitrile derivative (starting compound). The solvents can be employed singly or in combination.

The reducing reaction can be performed by causing formic acid and water into contact with the quinolylacrylonitrile derivative in a liquid phase in the presence of Raney-nickel. For instance, the reaction can be carried out by heating and stirring a mixture of the Raney-nickel, quinolylacrylonitrile derivative, formic acid and water at an atmospheric pressure or increased pressure under inert gas atmosphere. The reaction is performed at a temperature of preferably 20 to 110° C., more preferably 30 to 80° C. The reaction can be controlled, if desired, by addition of an inorganic base, an organic base, or a platinum salt to the reaction mixture, as described on pages 123–147 of "Raney Catalysts", Teruo Kubomatu and Shinichiro Komatsu, published by Kawaken Fine Chemicals Co., Ltd.

The reaction product (target product) of the reaction of the invention, that is, the quinolylpropenal derivative of the formula (2) can be isolated and purified after the reaction and subsequent filtration and extraction are complete, by a conventional procedure such as distillation, recrystallization, or column chromatography.

Another embodiment of the reducing reaction using Raney-nickel according to the present invention can be performed in the presence of an amine salt of formic acid and an organic acid.

The amine salt of formic acid is a salt formed of formic acid and an amine. Examples include ammonium formate; salts of formic acid with a primary amine such as monomethylammonium formate and monoethylammonium formate; salts of formic acid with a secondary amine such as dimethylarnonium formate and diethylammonium formate; and salts of formic acid with a tertiary amine such as trimethylammonium formate and triethylammonium formate. Preferred are ammonium formate and triethylammonium formate. More preferred is ammonium formate. The amine salt of formic acid is employed in an amount of preferably 1.0 to 5.0 moles, more preferably 1.5 to 3.0 moles, per one mole of the quinolylacrylonitrile derivative (starting compound).

The organic acid preferably is a lower aliphatic acid having 2 to 5 carbon atoms. Examples are acetic acid, propionic acid, butyric acid, isobutyric acid, valeric acid, isovaleric acid and pivalic acid. Preferred is acetic acid. The organic acid is employed in an amount of preferably 3 to 50 weight parts, more preferably 5 to 30 weight parts, per one weight part of the quinolylacrylonitrile derivative (starting compound). The organic acids can be employed singly or in combination.

The reducing reaction can be preferably performed by causing the quinolylacrylonitrile derivative of the formula (1) into contact with the amine salt of formic acid in an organic acid in the presence of Raney-nickel. For instance, the reaction can be carried out by heating and stirring a mixture of the Raney-nickel, quinolylacrylonitrile derivative, ammonium formate and an organic acid at an atmospheric pressure or increased pressure under inert gas atmosphere. The reaction is performed at a temperature of preferably 20 to 110° C., more preferably 40 to 90° C. The reaction can be controlled, if desired, by addition of an inorganic base, an organic base, or a platinum salt to the reaction mixture, as described on pages 123–147 of "Raney Catalysts", Teruo Kubomatu and Shinichiro Komatsu, published by Kawaken Fine Chemicals Co., Ltd.

The reaction product (target product) of the reaction of the invention, that is, the quinolylpropenal derivative of the formula (2) can be isolated and purified after the reaction and subsequent filtration and extraction are complete, by a conventional procedure such as distillation, recrystallization, or column chromatography.

Reference Example 1

Preparation of 3-[2-cyclopropyl-4-(4-fluorophenyl)-3-quinolyl]prop-2-enenitrile

In a 100 mL-volume glass flask equipped with a stirrer, a thermometer and a dropping funnel were placed under argon atmosphere 4.98 g (17.1 mmol) of 2-cyclo-propyl-4-(4-fluorophenyl)quinoline-3-carbaldehyde, 3.10 mL (18.8 mmol) of diethylcyanomethyl phosphonate (purity 98%), 0.15 mL (0.33 mmol) of tricaprilmethylammonium chloride (Aliquat 336, available from Aldrich Corp.), and 35 mL of toluene. To the content kept at 25–35° C. (liquid temperature) was slowly added 10.1 g (50.5 mmol) of aqueous sodium hydroxide solution (20 wt. %), and the mixture was reacted for 3 hours at the same temperature. Subsequently, 0.14 mL (0.85 mmol) of diethyl (cyanomethyl)-phosphonate (purity 98%) was added, and the mixture was reacted for 66 hours at the same temperature. After the reaction was complete, 5 mL of water was added to the reaction mixture, and the mixture was stirred for 30 minutes. To the mixture was added 50 mL of toluene, and the organic portion is taken out. The organic portion was washed with 10 mL of an aqueous sodium hydroxide solution (10 wt. %), and to the washed portion was added 10 mL of saturated aqueous sodium chloride solution. The aqueous mixture was neutralized by addition of 5.6 mL of hydrochloric acid (1 mol/L)., and the organic portion was taken out. The organic portion was placed in a 200 mL-volume glass flask equipped with a stirrer. To the organic portion was added 1.60 g of anhydrous sodium sulfate, and the mixture was stirred for one hour at room temperature. To the mixture were further added 0.14 g of active carbon (powder, available from Wako Junyaku Co., Ltd.) and 0.62 g of silica gel (Wakogel C-200, available from Wako Junyaku Co., Ltd.). The mixture was then stirred for 1.75 hours at room temperature, and filtered. through a celite. The celite was washed with 50 mL of toluene. The reaction liquid was concentrated under reduced pressure to precipitate a crystalline product. The crystalline product was heated to melt, and after addition of 30 mL of hexane, heated under reflux for 30 minutes. Thereafter, the liquid was chilled to 5° C., and stirred for 2 hours to precipitate a crystalline product. The crystalline product was collected by filtration, washed with 30 mL of hexane, and dried at 55° C. under reduced pressure, to obtain 4.81 g (yield 90%) of 3-[2-cyclopropyl-4-(4-fluorophenyl)-3-quinolyl]prop-2-enenitrile as a white crystalline product.

The obtained 3-[2-cyclopropyl-4-(4-fluorophenyl)-3-quinolyl]prop-2-enenitrile quinolyl] prop-2-enenitrile had the following characteristics:

m.p.: 175–176° C., EI-MS(m/e): 313(M-1), CI-MS(m/e): 315(M+1)

EXAMPLE 1

Preparation of 3-[2-cyclopropyl-4-(4-fluorophenyl)-3-quinolyl]prop-2-enal

In a 5 mL-volume glass flask equipped with a stirrer, a thermometer and a dropping funnel were placed under nitrogen atmosphere 314 mg (1.0 mmol) of 3-[2-cyclopropyl-4-(4-fluorophenyl)-3-quinolyl]prop-2-enenitrile (prepared in Reference Example 1), 2.25 mL of formic acid (60 mmol, mol calculated as 100% formic acid), 0.75 mL of water, and 620 mg (5.3 mmol as nickel atom) of water-containing developed Raney-nickel (NDHT-90, nickel content 50 wt. %, available from Kawaken Fine Chemical Co., Ltd.). The content was reacted at 80° C. for hours. After the reaction was complete, the content was cooled to room temperature. After addition of 9 mL of water and 9 mL of hydrochloric acid (1 mol/L), the catalyst was removed by filtration using a celite. The celite was washed with two portions of 2-butanol (1 mL) and two portions of toluene (9 mL). The organic portion was dried over anhydrous magnesium sulfate. The dried organic portion was filtered and the filtrate was concentrated under reduced pressure to give 307 mg (yield 91%) of 3-[2-cyclopropyl-4-(4-fluorophenyl)-3-quinolyl]prop-2-enal as yellow solid (purity 97%, in terms of an area percent according to high performance liquid chromatography).

The obtained 3-[2-cyclopropyl-4-(4-fluorophenyl)-3-quinolyl]prop-2-enal had the following characteristics:

CI-MS(m/e): 318(M+1)

$^1$H-NMR (CDCl$_3$, δ(ppm)): 1.07–1.13 (2H, m), 1.40–1.45 (2H, m), 2.32–2.37 (1H, m), 6.43 (1H, dd, J=7.5, 16.2 Hz), 7.22–7.26 (4H, m), 7.35–7.38 (2H, m), 7.55 (1H, d, J=16.2Hz), 7.64–7.69 (1H, m), 7.97 (1H, d, J=8.4Hz), 9.51 (1H, d, J=7.5 Hz).

EXAMPLE 2

The procedures of Example 1 were repeated except that the reaction was carried out at 65° C. for 5 hours, to give 3-[2-cyclopropyl-4-(4-fluorophenyl)-3-quinolyl]prop-2-enal (yield 83%).

EXAMPLE 3

The procedures of Example 1 were repeated except that the amount of formic acid and the amount of water were changed, respectively, to 1.8 mL and 1.2 mL, to give 3-[2-cyclopropyl-4-(4-fluorophenyl)-3-quinolyl]prop-2-enal (yield 91%).

EXAMPLE 4

The procedures of Example 2 were repeated except that the amount of formic acid and the amount of water were changed, respectively, to 2.55 mL and 0.45 mL, to give 3-[2-cyclopropyl-4-(4-fluorophenyl)-3-quinolyl]prop-2-enal (yield 85%).

Comparison Example 1

The procedures of Example 2 were repeated except that the amount of formic acid and the amount of water were changed, respectively, to 1.2 mL and 1.8 mL, to give 3-[2-cyclopropyl-4-(4-fluorophenyl)-3-quinolyl]prop-2-enal (yield 70%).

EXAMPLE 5

Preparation of 3-[2-cyclopropyl-4-(4-fluorophenyl)-3-quinolyl]prop-2-enal

In a 200 mL-volume glass flask equipped with a stirrer, a thermometer and a dropping funnel were placed under nitrogen atmosphere 4.0 g (12.7 mmol) of 3-[2-cyclopropyl-4-(4-fluorophenyl)-3-quinolyl]prop-2-enenitrile (prepared in Reference Example 1), 1.6 g (25.4 mmol) of ammonium formate, 4.4 g (37.5 mmol as nickel atom) of water-containing developed Raney-nickel (NDHT-90, nickel content 50 wt. %, available from Kawaken Fine Chemical Co., Ltd.), and 40 mL of acetic acid. The content was reacted at 65° C. for 4 hours. After the reaction was complete, the content was cooled to room temperature. After addition of 20 mL of ethanol, the catalyst was removed by filtration using a celite. The filtrate was concentrated under reduced pressure, and 40 mL of ethyl acetate was added. The mixture was washed successively with 5 mL of hydrochloric acid (1 mol/L), 10 mL of water, 20 mL of aqueous sodium hydroxide solution (1 mol/L), 14 mL of an aqueous alkaline DL-tartaric acid solution (1.0 g of DL-tartaric acid was dissolved in 1 mol/L aqueous sodium hydroxide solution), and 20 mL of saturated aqueous sodium chloride solution. The organic portion was dried over anhydrous magnesium sulfate. The organic portion was filtered and concentrated under reduced pressure, to obtain 3.4 g (yield 82%) of 3-[2-cyclopropyl-4-(4-fluorophenyl)-3-quinolyl]prop-2-enal as a pale yellow crystalline product (purity 98%, in terms of an area percent according to high performance liquid chromatography).

The obtained 3-[2-cyclopropyl-4-(4-fluorophenyl)-3-quinolyl]prop-2-enal had the characteristics essentially equivalent to those described in Example 1.

INDUSTRIAL APPLICABILITY

According to the preparation method of the invention, a quinolylpropenal derivative of the aforementioned formula (2) can be prepared from a quinolylacrylonitrile derivative of the aforementioned formula (1) in a simple procedure. Accordingly, the invention provides an industrially advantageous method of producing a quinolylacrolein.

What is claimed is:

1. A method for preparing 3-[2-cyclopropyl-4-(4-fluorophenyl)-3-quinolyl]prop-2-enal by reducing 3-[2-cyclopropyl-4-(4-fluorophenyl)-3-quinolyl]prop-2-enenitrile using Raney-nickel in the presence of formic acid and water in an amount of 0.25 to 1 volume part per one volume part of the formic acid, or in the presence of an amine salt of formic acid and an organic acid.

2. The method of claim 1, wherein the Raney-nickel is employed in an amount of 0.30 to 2 weight parts in terms of weight of nickel atom, per one weight part of 3-[2-cyclopropyl-4-(4-fluorophenyl)-3-quinolyl]prop-2-enenitrile.

3. The method of claim 1, wherein the 3-[2-cyclo-propyl-4-(4-fluorophenyl)-3-quinolyl]prop-2-enenitrile is reduced by the Raney-nickel in the presence of 0.25 to 50 weight parts of formic acid per one weight part of the enenitrile and 0.25 to 1 volume part of water per one volume part of the formic acid.

4. The method of claim 1, wherein the 3-[2-cyclo-propyl-4-(4-fluorophenyl)-3-quinolyl]prop-2-enenitrile is reduced by the Raney-nickel in the presence of ammonium formate and an organic acid.

5. The method of claim 4, wherein the organic acid is employed in an amount of 3 to 50 weight parts per one weight part of the enenitrile.

6. The method of claim 1, wherein the 3-[2-cyclo-propyl-4-(4-fluorophenyl)-3-quinolyl]prop-2-enenitrile is reduced by the Raney-nickel in the presence of an amine salt of formic acid and a lower-aliphatic acid having 2 to 5 carbon atoms.

7. The method of claim 6, wherein the amine salt of formic acid is employed in an amount of 1.0 to 5.0 moles per one mole of the enenitrile.

8. The method of claim 1, wherein the 3-[2-cyclo-propyl-4-(4-fluorophenyl)-3-quinolyl]prop-2-enenitrile is reduced by the Raney-nickel in the presence of an ammonium formate and a lower aliphatic acid having 2 to 5 carbon atoms.

9. The method of claim 1, wherein the reduction using Raney-nickel is performed at a temperature in the range of 20 to 110° C.

* * * * *